US012773207B2

(12) United States Patent
Larsen

(10) Patent No.: US 12,773,207 B2
(45) Date of Patent: Oct. 27, 2026

(54) SUTURE-BASED REPAIR

(71) Applicant: DePuy Synthes Products, Inc., Raynham, MA (US)

(72) Inventor: Scott Joseph Larsen, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 299 days.

(21) Appl. No.: 18/488,266

(22) Filed: Oct. 17, 2023

(65) Prior Publication Data

US 2024/0130726 A1 Apr. 25, 2024
US 2024/0225638 A9 Jul. 11, 2024

Related U.S. Application Data

(60) Provisional application No. 63/380,621, filed on Oct. 24, 2022.

(51) Int. Cl.

| | |
|---|---|
| ***A61B 17/04*** | (2006.01) |
| ***A61B 17/06*** | (2006.01) |
| ***A61F 2/42*** | (2006.01) |

(52) U.S. Cl.

CPC .... *A61B 17/06166* (2013.01); *A61B 17/0401* (2013.01); *A61F 2/4241* (2013.01); *A61B 2017/0404* (2013.01); *A61B 2017/044* (2013.01); *A61F 2002/4258* (2013.01)

(58) Field of Classification Search

CPC .................. A61F 2/4241; A61F 2/0811; A61F 2002/4253; A61F 2002/4258; A61B 17/0401; A61B 17/06166; A61B 2017/044; A61B 2017/0475; A61B 17/1782; A61B 17/1775; A61B 2017/564; A61B 2017/0404; A61B 2017/0414

See application file for complete search history.

(56) References Cited

U.S. PATENT DOCUMENTS

| | | | |
|---|---|---|---|
| 5,573,286 | A | 11/1996 | Rogozinski |
| 8,388,654 | B2 | 3/2013 | Snyder et al. |
| 8,608,758 | B2 | 12/2013 | Singhatat et al. |
| 8,784,449 | B2 | 7/2014 | Snyder et al. |
| 8,876,840 | B2 | 11/2014 | Harada et al. |
| 8,961,575 | B2 | 2/2015 | Choinski |
| 8,979,873 | B2 | 3/2015 | Singhatat et al. |
| 9,039,739 | B2 | 5/2015 | Rohlinger et al. |
| 9,144,424 | B2 | 9/2015 | Snyder et al. |
| 9,320,514 | B2 | 4/2016 | Rohlinger et al. |

(Continued)

OTHER PUBLICATIONS

Arthrex CMC Ligament Reconstruction, YouTube video, accessed online Oct. 26, 2023, https://www.youtube.com/watch?v=xOWu0r5Fa7w.

(Continued)

*Primary Examiner* — Katherine M Shi
(74) *Attorney, Agent, or Firm* — BakerHostetler

(57) ABSTRACT

Provided herein are methods, constructs, and kits for positioning a first bone segment relative to a second bone segment within a subject's body, for example, in order to establish a reduced position of the first and second bone segments. The present disclosure provides, among other things, alternatives to traditional ligament reconstruction and tendon interposition (LRTI) and suture suspension arthroplasty procedures.

17 Claims, 4 Drawing Sheets

(56) References Cited

U.S. PATENT DOCUMENTS

| | | | | |
|---|---|---|---|---|
| 9,451,938 | B2 | 9/2016 | Overes et al. | |
| 9,452,058 | B2 | 9/2016 | Jou et al. | |
| 9,597,064 | B2 | 3/2017 | Overes et al. | |
| 9,707,090 | B2 | 7/2017 | DelSignore | |
| 9,713,464 | B2 | 7/2017 | Overes et al. | |
| 9,724,080 | B2 | 8/2017 | Corrao et al. | |
| 9,743,919 | B2 | 8/2017 | Manos et al. | |
| 9,763,719 | B2 | 9/2017 | Snyder et al. | |
| 9,826,969 | B2 | 11/2017 | Larsen | |
| 9,883,859 | B2 | 2/2018 | Conley et al. | |
| 10,595,839 | B2 | 3/2020 | Corrao et al. | |
| 10,820,894 | B2 | 11/2020 | Overes et al. | |
| 11,116,492 | B2 | 9/2021 | Overes et al. | |
| 2006/0190042 | A1 | 8/2006 | Stone et al. | |
| 2007/0083236 | A1 | 4/2007 | Sikora et al. | |
| 2009/0276055 | A1 | 11/2009 | Harris et al. | |
| 2010/0016892 | A1* | 1/2010 | Kaiser ................ | A61B 17/0401 606/232 |
| 2012/0143215 | A1* | 6/2012 | Corrao ............... | A61B 17/0482 606/151 |
| 2013/0172893 | A1* | 7/2013 | Gordon .............. | A61B 17/0401 606/232 |
| 2013/0245700 | A1* | 9/2013 | Choinski ............ | A61B 17/0401 606/300 |
| 2014/0128984 | A1 | 5/2014 | Jou et al. | |
| 2017/0181739 | A1* | 6/2017 | Breslich ............. | A61B 17/0401 |
| 2017/0231619 | A1 | 8/2017 | Bojarski et al. | |
| 2018/0021124 | A1 | 1/2018 | Champagne et al. | |
| 2018/0303475 | A1* | 10/2018 | Sengun .............. | A61B 17/0401 |
| 2019/0015091 | A1 | 1/2019 | Guo et al. | |
| 2019/0117210 | A1 | 4/2019 | Fleischman et al. | |
| 2020/0093482 | A1 | 3/2020 | Bruker et al. | |
| 2020/0107840 | A1 | 4/2020 | Summitt et al. | |

OTHER PUBLICATIONS

Arthrex, The Arthrex Mini TightRope Implant, Surgical Technique, https://www.arthrex.com/resources/VID1-00185-EN/the-arthrex-mini-tightrope-implant, accessed on Oct. 26, 2023.

* cited by examiner

SUTURE-BASED REPAIR

CROSS-REFERENCE TO RELATED APPLICATIONS

The present application claims the benefit of priority to U.S. Provisional Application No. 63/380,621, filed Oct. 24, 2022, the entire contents of which are incorporated herein by reference.

TECHNICAL FIELD

The present disclosure relates to strategies for effecting a reduced position between bone segments, including carpometacarpal repair.

BACKGROUND

Osteoarthritis (OA) of the thumb trapeziometacarpal (TMC) joint is a common disabling condition. Trapeziectomy may be used used for decreasing pain and improving hand use and function in patients with carpometacarpal joint osteoarthritis. In order to obtain long-term stability at the base of the thumb after trapeziectomy, it may be advisable to perform ligament reconstruction. This is commonly achieved using the ligament reconstruction and tendon interposition (LRTI) procedure. Using this approach, piece of tendon from one of the wrist muscles (the flexor carpi radialis) is cut, and part of the cut tendon is used to reconstruct the ligament that used to connect the metacarpal bone to the trapezium. The remaining portion of the tendon is then folded and used to fill the space formerly occupied by the trapezium.

A further approach for stabilizing the relative positions of the first and second metacarpals is suture suspension arthroplasty (SSA). This technique uses a single incision, trapeziectomy, and an intra-articular suture suspension sling anchored into the insertions of the flexor carpi radialis (FCR) and abductor pollicis longus (APL), which serves to stabilize the base of the thumb metacarpal, correct subluxation deformity, and maintain arthroplasty space.

Both the LRTI and SSA procedures can involve harvesting all or part of the FCR tendon, which has implications for the complexity of the reparative procedure and for the length of the post-operative recovery period.

SUMMARY

Provided herein are methods for positioning a first bone segment relative to a second bone segment within a subject's body comprising securing at least a part of a middle portion of a suture construct to the second bone segment, wherein the suture construct further includes a loop arm and a free arm positioned such that the middle portion extends from the loop arm to the free arm, and a suture loop at a terminal end of the loop arm; passing one of the free arm and the loop arm through a hole in the first bone segment; passing the free arm through the suture loop of the loop arm; and sliding the suture loop along the free arm toward the first bone segment so as to draw together the first bone segment and the second bone segment to establish a reduced position of the first bone segment and the second bone segment.

Also provided are suture constructs for positioning a first bone segment relative to a second bone segment within a subject's body comprising a loop arm, a free arm, and a middle portion that extends from the loop arm to the free arm, the loop arm comprising a suture loop at the terminal end of the loop arm, and a sliding joint positioned at a juncture between the suture loop and a linear portion of the loop arm.

Also disclosed are kits for securing a position of a first bone segment relative to a second bone segment within a subject's body comprising a suture construct according to the preceding embodiment; and, an interposition material for attachment to the suture construct by threading the loop arm or the free arm through the interposition material.

DETAILED DESCRIPTION OF ILLUSTRATIVE EMBODIMENTS

Figure 1A:
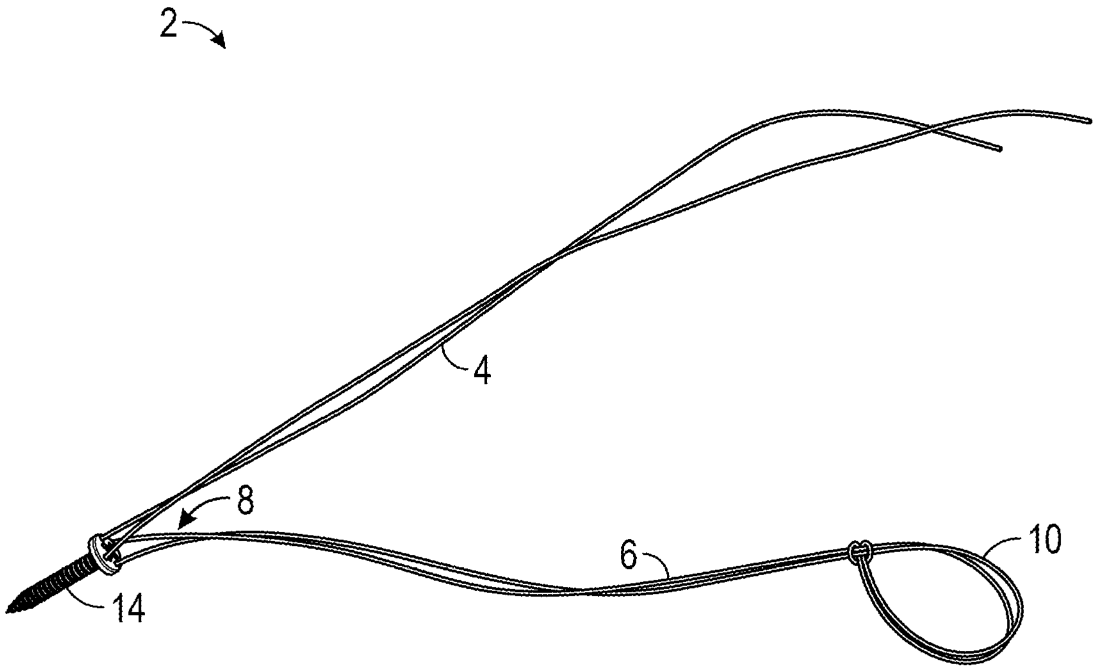
FIGS. 1A and 1B show exemplary suture constructs according to the present disclosure.

The presently disclosed inventive subject matter may be understood more readily by reference to the following detailed description taken in connection with the accompanying figures and examples, which form a part of this disclosure. It is to be understood that these inventions are not limited to the specific products, methods, conditions or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "an anchor" is a reference to one or more of such anchors and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably refers to a value of 7.2% to 8.8%, inclusive. Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included." The phrase "at least about x" is intended to embrace both "about x" and "at least x". It is also understood that where a parameter range is provided, all integers within that range, and tenths thereof, are also provided by the invention. For example, "2-5 hours" includes 2 hours, 2.1 hours, 2.2 hours, 2.3 hours, etc., up to 5 hours.

Removal of the trapezium (trapeziectomy) for can be effective for addressing osteoarthritis at the base of the thumb (trapeziometacarpal osteoarthritis). However, trapeziectomy partly disrupts the constraints of the scaphotrapeziotrapeziod (STT) joint, which has been suggested to potentially cause a carpal instability pattern that has been termed as non-dissociative. In dissociative carpal instability, there is a disruption of intrinsic intercarpal ligaments causing instability between bones within the same carpal row. It has presently been discovered that a suture-based approach as described herein can be used to effect a reduced position between bone segments, including metacarpal members, in order to increase the stability of the relative positions of such segments.

Accordingly, provided herein are methods for positioning a first bone segment relative to a second bone segment within a subject's body comprising securing at least a part of a middle portion of a suture construct to the second bone segment, wherein the suture construct further includes a loop arm and a free arm positioned such that the middle portion extends from the loop arm to the free arm, and a suture loop at a terminal end of the loop arm; passing one of the free arm and the loop arm through a hole in the first bone segment; passing the free arm through the suture loop of the loop arm; and sliding the suture loop along the free arm toward the first bone segment so as to draw together the first bone segment and the second bone segment to establish a reduced position of the first bone segment and the second bone segment.

Pursuant to the present methods, the first bone segment and the second bone segment may be of the same bone. In other words, the method may be for positioning a first bone segment that represents a first portion of a bone relative to a second bone segment that represents a second portion of the same bone. Such a process may be used, for example, in the situation in which a bone has been fractured and it is desirable to establish a reduced position between portions of the bone that were separated as a result of the fracture.

In other embodiments, the first bone segment and the second bone segment are of different bones. For example, it may be desirable to reduce the distance between respective bones that, under normal physiological circumstances, are in a particular position relative to one another, but that have deviated from this position, or to maintain the positions of the respective bones relative to one another if they have not yet deviated from the correct physiological positioning but there is a risk that they could do so. In certain embodiments, the bone segments are both bones within the human hand, such as a situation in which the first bone segment and the second bone segment are both metacarpals. For example, the first bone segment may be the first metacarpal bone, and the second bone segment may be the second metacarpal bone.

Figure 1B:
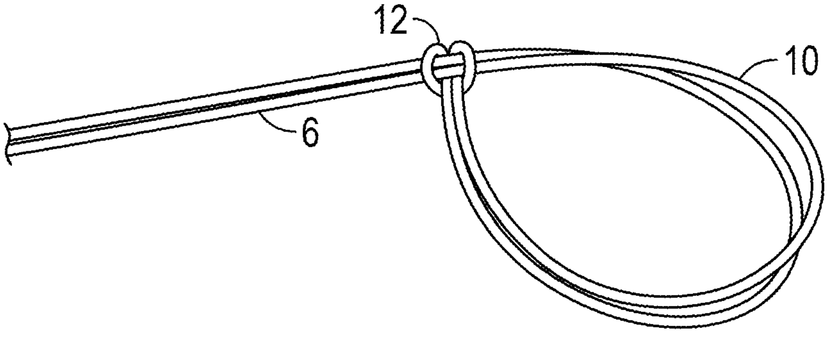

The suture construct that is used in the present methods includes a loop arm and a free arm that are respectively positioned such that a middle portion of the suture construct extends from the loop arm to the free arm. The suture construct further includes a suture loop at a terminal end of the loop arm. FIG. 1A shows an exemplary suture construct 2 according to the present disclosure, including a free arm 4, a loop arm 6 that includes a suture loop 10 at a terminal end of loop arm 6, and a middle portion 8 that extends from the loop arm 6 to the free arm 4. As shown in FIG. 1B, the suture construct 2 may further include a sliding joint 12 that is positioned at a juncture between the suture loop 10 and a linear portion of the loop arm 6. In FIG. 1B, the sliding joint 12 is a knot. U.S. Pat. No. 9,826,969, which is incorporated herein by reference, discloses an adjustable suture knot that includes a sliding knot, shown as reference numeral 12 in FIG. 1 of the patent, that may be used for the sliding joint in accordance with the present disclosure. In other embodiments, the sliding joint 12 may include a suture button. Any mechanism or component that enables the sliding joint to move along loop arm 6 in order to expand or contract the suture loop may be used.

The suture construct may be formed from suture thread, suture tape, cable, or any combination thereof. In certain embodiments, the suture construct is formed from suture thread. One or more of the loop arm, free arm, and middle portion can comprise, one, two, or more than two suture strands.

At least a part of the middle region of the suture construct is secured to the second bone segment pursuant to the present methods. As shown in FIG. 1A, a portion of the middle region 8 of the suture construct 2 is attached to a suture anchor 14. In the embodiment shown in FIG. 1A, each of the free arm 4, middle region 8, loop arm 6, and suture loop 10 comprise two suture strands. The suture anchor 14 may be used to secure the middle region 8 to the second bone segment. Any type of suture anchor may be used. For example, the suture anchor may include an anchor portion that is threaded or that provides and interference fit. The suture anchor may comprise any biocompatible material, and may be resorbable, non-resorbable, or partially resorbable.

Figure 2A:
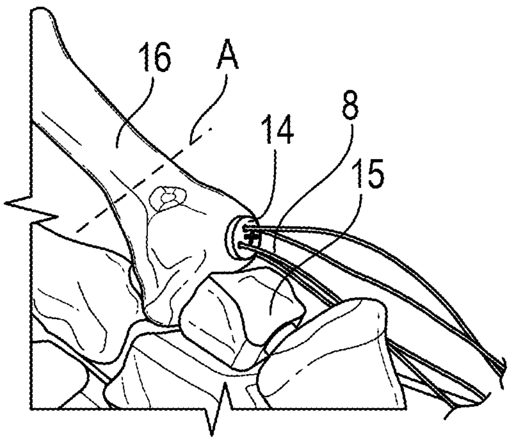
FIGS. 2A-2G illustrate how the present methods for positioning a first bone segment relative to a second bone segment within a subject's body are performed.

FIG. 2A depicts a suture anchor 14 through which the middle region 8 of a suture construct has been passed, the suture anchor 14 being secured to a second metacarpal bone 16. In some embodiments, the middle portion of the suture construct is secured to a location on the second metacarpal bone that is below line A as shown in FIG. 2A, i.e., that is more proximate to the trapezoid bone 15 than to the proximal phalanx bone (not shown) of the second metacarpal 16. For example, as in FIG. 2A, the middle portion of the suture construct may be secured to the second metacarpal facet of the second metacarpal bone.

Figure 2B:
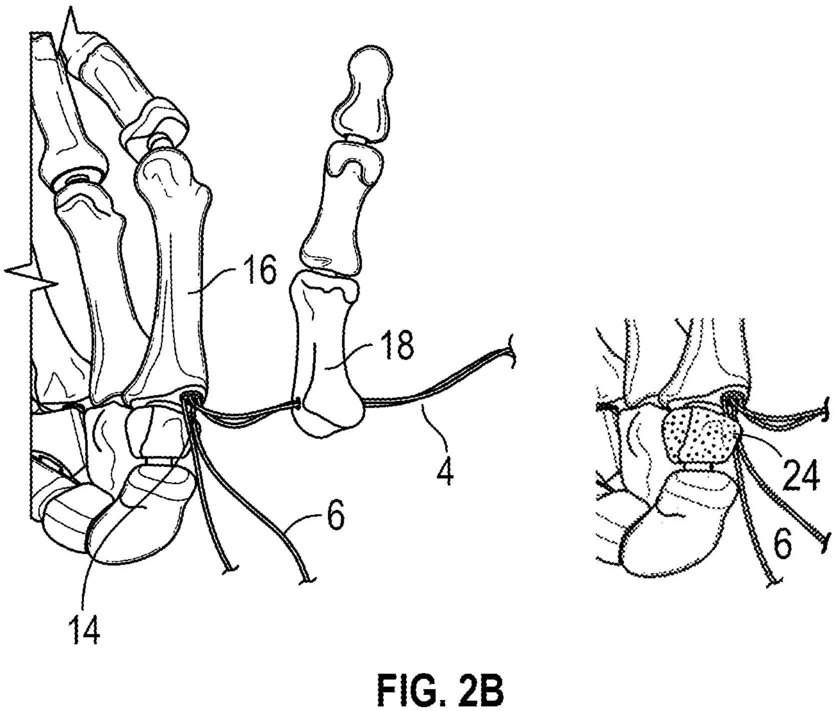

The securing step may be performed prior to or following a step in which either the free arm or the loop arm of the suture construct is passed through a hole in the first bone segment. FIG. 2B shows a situation in which the free arm 4 has been passed through a hole (not visible) in a first bone segment 18 representing a first metacarpal bone, and a portion of the middle region 8 has been secured to a second metacarpal bone 16 using a suture anchor 14.

Figure 2C:
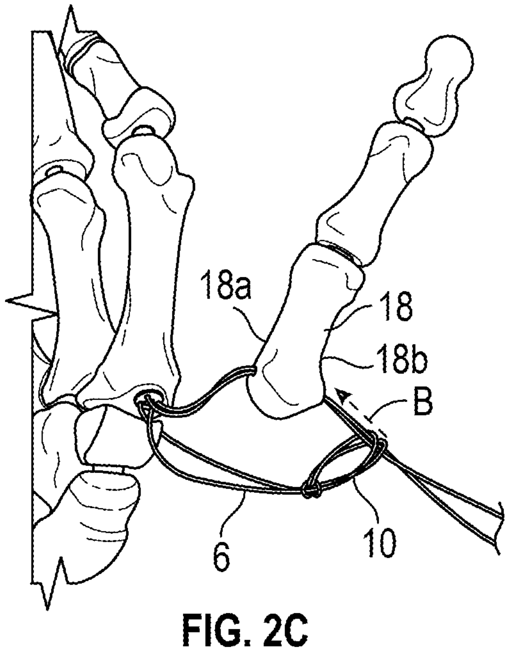
Figure 2D:
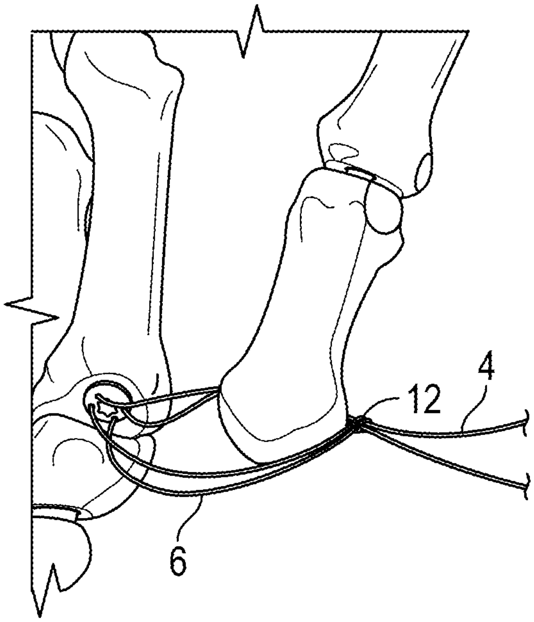

After the free arm or the loop arm is passed through a hole in the first bone segment, the free arm is passed through the suture loop of the loop arm. FIG. 2C depicts an arrangement in which the free arm 4 of the suture construct has been passed through the suture loop 10 of the loop arm 6. Following the step of passing the free arm through the suture loop, the suture loop is optionally contracted around the free arm. This may be accomplished by sliding the suture joint (e.g., a knot or button) towards the free arm. FIG. 2D shows a situation in which the suture loop (no longer visible) of the loop arm 6 has been fully contracted around the free arm 4 by sliding the suture joint 12.

Figure 2G:
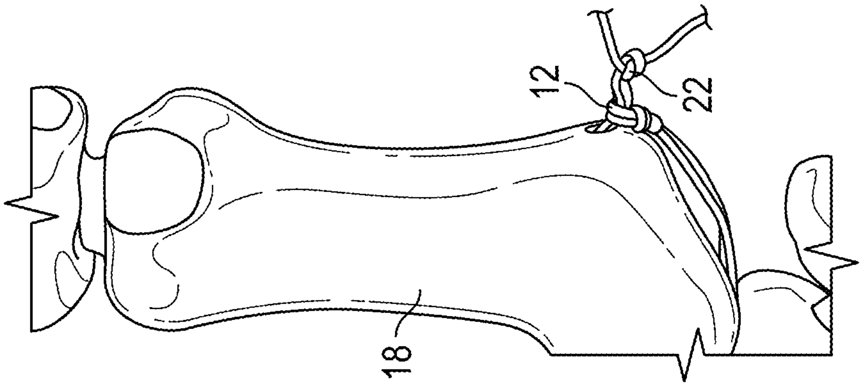
Figure 2F:
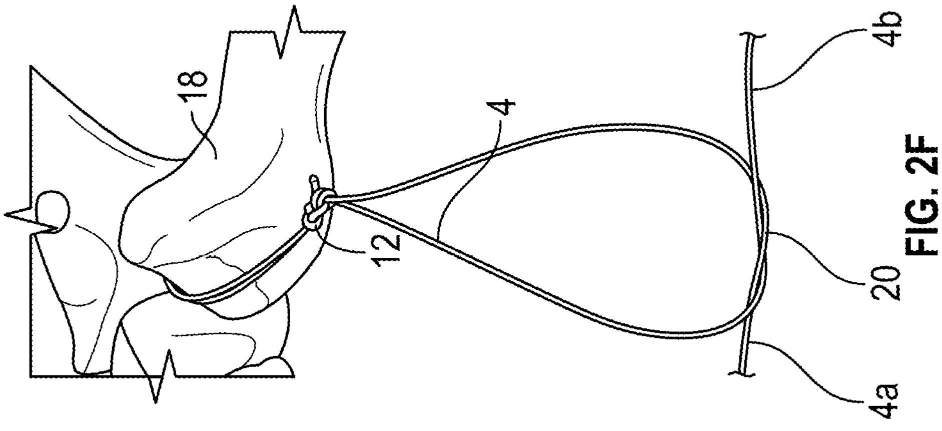
Figure 2E:
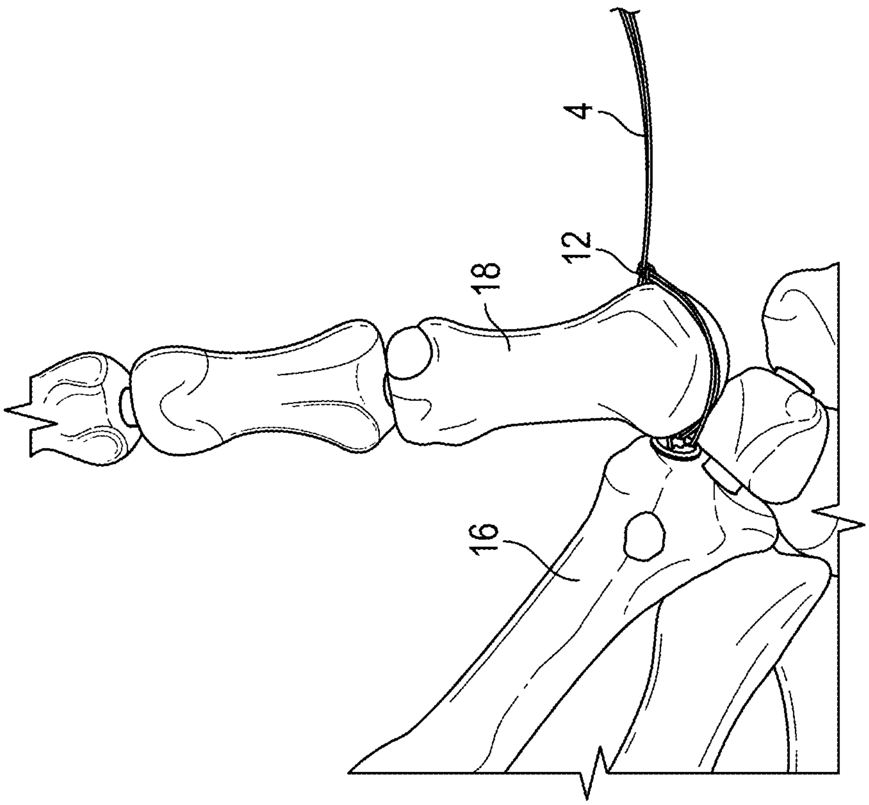

After the free arm is passed through the suture loop of the loop arm, the suture loop is slid along the free arm toward the first bone segment. Doing so draws together the first bone segment and the second bone segment in order to establish a reduced position of the first bone segment and the second bone segment. In some embodiments, as shown in FIG. 2C, the hole in the first bone segment 18 extends from a first side 18*a* of the first bone segment to an opposed second side 18*b* of the first bone segment, and the second passing step, i.e., the step of passing the free arm through the suture loop of the loop arm, comprises sliding the suture loop along the free arm toward the second side of the first bone segment, i.e., in the direction of arrow B. The extent of the sliding of the suture loop along the free arm, and the extent of the drawing together of the first and second bone segments can both be determined by a practitioner (e.g., a surgeon), who will assess whether the respective extents are therapeutically appropriate. For example, the extent of the drawing together of the first and second bone segments can be that which is determined by a surgeon to be what approximates the anatomically appropriate positioning of the first and second bone segments relative to each other. In some embodiments, the suture loop is slid along the free arm until it contacts the first bone segment. This condition is shown in FIG. 2E: the contracted suture loop, visible only as suture joint 12, has slid along free arm 4 until it contacts first bone segment 18 (as shown, the first metacarpal bone). In the embodiment shown in FIG. 2E, the first bone segment 18 has been drawn closer to second bone segment 16, such that the respective bone segments substantially contact one another.

The present methods may further comprise a step of securing the first bone segment relative to the second bone segment in the reduced position. In some embodiments, this can include forming a knot using the free arm proximate to a location where the suture loop engages the free arm. FIG. 2F shows the preparation of a half-hitch knot 20 using the two suture strands 4*a*, 4*b* forming the free arm 4. As knot 20 is tightened, it is drawn up against suture knot 12, i.e., where the suture loop (no longer visible) engages the free arm. FIG. 2G depicts a situation in which a series of knots 22 (e.g., half-hitch knots) are formed proximate to the location where the suture loop in the form of suture knot 12 engages the free arm. The knots 22 serve to secure the first bone segment 18 relative to the second bone segment in the reduced position. Following the step of securing the first bone segment relative to the second bone segment in the reduced position, the loose strands 4*a* and 4*b* of free arm 4 may be cut, e.g., as in FIG. 4G, the loose strands that extend from knots 22 may be cut.

As described previously herein, the ligament reconstruction and tendon interposition (LRTI) procedure involves folding a portion of the flexor carpi radialis (FCR) tendon in order to fill the void space formerly occupied by the trapezium. In accordance with the present disclosure, as an alternative to the use of the FCR tendon, a portion of the suture construct may be threaded through an interposition material that can serve to occupy at least a portion of a space that results from the excision of a trapezium bone. In FIG. 2B, the right-hand panel depicts interposition material 24 replacing the natural trapezium bone, and through which loop arm 6 has been threaded. The interposition material is intended to provide the structural support and enable the positioning among the remaining bones of the hand in the manner provided by the trapezium before its removal. In this sense, the interposition material can eliminate the need for a K-wire fixation process. The interposition material preferably includes elements that promote the formation of scar tissue at the location of the material. Exemplary interposition materials that can be used in accordance with the present disclosure are described in U.S. Provisional Application No. 63/66,563, filed on Jun. 17, 2022, which is incorporated herein by reference in its entirety. As noted above, one of the free arm or the loop arm is passed through a hole that is formed through the first bone segment, and, pursuant to embodiments in which an interposition material is used, the other of the free arm or the loop arm (i.e., the portion of the suture construct that is not passed through the hole in the first bone segment) can be threaded through the interposition material in order to secure the latter at a desired location within the space formerly occupied by the trapezium. Optionally, the arm may be threaded through the interposition material prior to securing the middle portion of the suture construct to the second bone segment, or may be threaded through the interposition material after securing the middle portion of the suture construct to the second bone segment.

The present disclosure also provides suture constructs for positioning a first bone segment relative to a second bone segment within a subject's body, comprising a loop arm, a free arm, and a middle portion that extends from the loop arm to the free arm, the loop arm comprising a suture loop at the terminal end of the loop arm, and a sliding joint positioned at a juncture between the suture loop and a linear portion of the loop arm. Any one or more of the characteristics of the suture constructs described supra in connection with the present methods may be included with respect to the inventive constructs.

Also provided herein are kits for securing a position of a first bone segment relative to a second bone segment within a subject's body comprising a suture construct according to any one of the embodiments described in the present disclosure; and, an interposition material as described supra for attachment to the suture construct by threading the loop arm or the free arm through the interposition material.

The present disclosure also pertains to and includes at least the following aspects:

Aspect 1. A method for positioning a first bone segment relative to a second bone segment within a subject's body comprising:

- securing at least a part of a middle portion of a suture construct to the second bone segment, wherein the suture construct further includes a loop arm and a free arm positioned such that the middle portion extends from the loop arm to the free arm, and a suture loop at a terminal end of the loop arm;
- passing one of the free arm and the loop arm through a hole in the first bone segment;
- passing the free arm through the suture loop of the loop arm; and
- sliding the suture loop along the free arm toward the first bone segment so as to draw together the first bone segment and the second bone segment to establish a reduced position of the first bone segment and the second bone segment.

Aspect 2. The method according to aspect 1, wherein the securing step is performed prior to the first passing step.

Aspect 3. The method according to aspect 1, wherein the securing step is performed after the first passing step.

Aspect 4. The method according to any preceding aspect, further comprising contracting the suture loop around the free arm following the step of passing the free arm through the suture loop.

Aspect 5. The method according to any preceding aspect, wherein the second passing step further comprises sliding the suture loop along the free arm until it contacts the first bone segment.

Aspect 6. The method according to any preceding aspect, wherein the hole extends from a first side of the first bone segment to an opposed second side of the first bone segment, and the second passing step comprises sliding the suture loop along the free arm toward the second side of the first bone segment.

Aspect 7. The method according to any preceding aspect, further comprising the step of securing the first bone segment relative to the second bone segment in the reduced position.

Aspect 8. The method according to aspect 7, wherein the securing first bone segment relative to the second bone segment in the reduced position comprises forming a knot using the free arm proximate to a location where the suture loop engages the free arm.

Aspect 9. The method according to any preceding aspect, wherein the middle portion of the suture construct is secured to the second bone segment using a suture anchor.

Aspect 10. The method according to any preceding aspect, wherein the suture construct is formed from suture thread.

Aspect 11. The method according to any one of aspects 1-9, wherein the suture construct is formed from suture tape.

Aspect 12. The method according to any preceding aspect, wherein the first bone segment and the second bone segment are of the same bone.

Aspect 13. The method according to any one of aspects 1-11, wherein the first bone segment and the second bone segment are of different bones.

Aspect 14. The method according to any preceding aspect, wherein the first bone segment is a first metacarpal bone, and the second bone segment is a second metacarpal bone.

Aspect 15. The method according to aspect 14, wherein the middle portion of the suture construct is secured to the second metacarpal facet of the second metacarpal bone.

Aspect 16. The method according to aspect 14 or aspect 15, wherein the other one of the free arm or the loop arm that is passed through the hole that is formed through the first bone segment is threaded through an interposition material for occupying at least a portion of a space that results from the excision of a trapezium bone.

Aspect 17. The method according to aspect 16, wherein the arm is threaded through the interposition material prior to securing the middle portion of the suture construct to the second bone segment.

Aspect 18. The method according to any preceding aspect, wherein each of the loop arm, free arm, and middle portion of the suture construct comprises two or more suture strands.

Aspect 19. A suture construct for positioning a first bone segment relative to a second bone segment within a subject's body comprising a loop arm, a free arm, and a middle portion that extends from the loop arm to the free arm, the loop arm comprising a suture loop at the terminal end of the loop arm, and a sliding joint positioned at a juncture between the suture loop and a linear portion of the loop arm.

Aspect 20. The suture construct according to aspect 19, further comprising a suture anchor to which the middle portion is affixed.

Aspect 21. The suture construct according to aspect 19 or aspect 20, wherein each of the loop arm, free arm, and middle portion comprises two or more suture strands.

Aspect 22. The suture construct according to any one of aspect 19-aspect 21, wherein the sliding joint comprises a knot.

Aspect 23. The suture construct according to any one of aspect 19-aspect 21, wherein the sliding joint comprises a suture button.

Aspect 24. The suture construct according to any one of aspects 19-23, wherein when the suture construct is used to position a first bone segment relative to a second bone segment, the middle portion is configured for being secured to the second bone segment.

Aspect 25. The suture construct according to any one of aspects 19-24, wherein when the suture construct is used to position a first bone segment relative to a second bone segment, at least one of the free arm and the loop arm are configured to be passed through a hole in the first bone segment.

Aspect 26. The suture construct according to aspect 25, wherein the free arm is configured to be passed through the suture loop of the loop arm after one of the free arm and the loop arm are passed through a hole in the first bone segment.

Aspect 27. The suture construct according to any one of aspects 19-26, wherein the sliding joint is configured for sliding along the free arm.

Aspect 28. The suture construct according to any one of aspects 19-27 comprising suture thread.

Aspect 29. A kit for securing a position of a first bone segment relative to a second bone segment within a subject's body comprising:
- a suture construct according to any one of aspects 19-28; and,
- an interposition material for attachment to the suture construct by threading the loop arm or the free arm through the interposition material.

Aspect 30. The kit according to aspect 29, further comprising a needle for driving the loop arm or the free arm through the interposition material.

Aspect 31. A construct for positioning a first bone segment relative to a second bone segment within a subject's body, the construct comprising:
- a middle portion of a suture construct that is configured to be secured to the second bone segment, wherein the suture construct further includes a loop arm and a free arm positioned such that the middle portion extends from the loop arm to the free arm, and a suture loop at a terminal end of the loop arm;
- at least one of the free arm and the loop arm being configured for being passed through a hole in the first bone segment;
- the free arm being configured for being passed through the suture loop of the loop arm; and
- the suture loop being configured for sliding along the free arm toward the first bone segment so as to draw together the first bone segment and the second bone segment to establish a reduced position of the first bone segment and the second bone segment.

EXAMPLES

The present invention is further defined in the following Examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

Example 1—Positioning a First Metacarpal Bone Relative to a Second Metacarpal A suture construct formed from a double strand of suture thread and comprising a loop arm, a free arm, a middle portion extending from the loop arm to the free arm, and a suture loop at a terminal end of the loop arm is secured to the second metacarpal facet of the second metacarpal bone of a female subject, aged 70, who has undergone trapeziectomy. In particular, the free arm of the suture construct is drawn through the eyelet of a suture anchor, such that the middle portion of the suture construct is positioned within the eyelet of the suture anchor. Using an orthopedic drill bit, a hole is drilled laterally into the lower portion of the second metacarpal bone at the location of the second metacarpal facet. The suture anchor is then driven into the second metacarpal facet, thereby securing the suture construct to the subjects second metacarpal bone.

A hole is formed through first metacarpal bone of the subject, whereby the hole extends from a first side of the first metacarpal bone to an opposed second side of the first metacarpal bone. The free arm of the suture construct is passed through the hole on the side of the first metacarpal bone that is anatomically proximate to the second metacarpal bone, and the free arm is then drawn out from the hole on the opposed side of the second metacarpal bone.

The free arm is passed through the suture loop of the loop arm, and the suture loop is then contracted around the free arm. The contracted suture loop is then slid along the free arm towards the first metacarpal until it contacts the first metacarpal. The contracted suture loop is slid further in the direction of the first metacarpal bone in order to urge the first metacarpal towards the second metacarpal, until the first metacarpal is in a position relative to the second metacarpal that is determined by the surgeon as representing the appropriate final positional relationship.

The strands of the free arm are formed into a series of half-hitch knots that secures the first metacarpal in the desired position relative to the second metacarpal, and the loose strands of the free arm are thereafter cut.

Example 2—Trapeziectomy and Implantation of Interposition Material

In the same manner as in Example 1, a suture construct is used to position a first metacarpal relative to a second metacarpal as deemed appropriate by a surgeon. However, following the step of passing the free arm through the hole in the first metacarpal and prior to the step of passing the free arm through the suture loop of the loop arm, the free arm is threaded through an interposition material. The interposition material, which comprises elements that allow infiltration of blood components, such as platelets, pursuant to the formation of scar tissue, is emplaced within the void space that resulted from the excision of the trapezium from the subject. After the free arm is threaded through the interposition material, the free arm is passed through the suture loop of the loop arm, and the remainder of the procedure for positioning the first metacarpal relative to the second metacarpal is the same as in Example 1. The interposition material, which is secured by the suture construct within the space formerly occupied by the subject's trapezium, is resorbed over the course of about six weeks.

What is claimed:

1. A method for positioning a first bone segment relative to a second bone segment within a subject's body comprising:

securing at least a part of a middle portion of a suture construct to the second bone segment, wherein the suture construct further includes a loop arm and a free arm positioned such that the middle portion extends from the loop arm to the free arm, and a suture loop at a terminal end of the loop arm;

a first passing step of passing one of the free arm and the loop arm through a hole in the first bone segment;

a second passing step of passing the free arm through the suture loop of the loop arm and sliding the suture loop along the free arm until it contacts the first bone segment; and sliding the suture loop along the free arm toward the first bone segment so as to draw together the first bone segment and the second bone segment to establish a reduced position of the first bone segment and the second bone segment.

2. The method according to claim 1, wherein the securing step is performed prior to the first passing step.

3. The method according to claim 1, wherein the securing step is performed after the first passing step.

4. The method according to claim 1, further comprising contracting the suture loop around the free arm following the step of passing the free arm through the suture loop.

5. The method according to claim 1, wherein the hole extends from a first side of the first bone segment to an opposed second side of the first bone segment, and the second passing step comprises sliding the suture loop along the free arm toward the second side of the first bone segment.

6. The method according to claim 1, further comprising the step of securing the first bone segment relative to the second bone segment in the reduced position.

7. The method according to claim 6, wherein the securing first bone segment relative to the second bone segment in the reduced position comprises forming a knot using the free arm proximate to a location where the suture loop engages the free arm.

8. The method according to claim 1, wherein the middle portion of the suture construct is secured to the second bone segment using a suture anchor.

9. The method according to claim 1, wherein the suture construct is formed from suture thread.

10. The method according to claim 1, wherein the suture construct is formed from suture tape.

11. The method according to claim 1, wherein the first bone segment and the second bone segment are of the same bone.

12. The method according to claim 1, wherein the first bone segment and the second bone segment are of different bones.

13. The method according to claim 1, wherein the first bone segment is a first metacarpal bone, and the second bone segment is a second metacarpal bone.

14. The method according to claim 13, wherein the middle portion of the suture construct is secured to the second metacarpal facet of the second metacarpal bone.

15. The method according to claim 13, wherein the subject's trapezium bone has been excised, and the other one of the free arm or the loop arm that is passed through the hole that is formed through the first bone segment is threaded through an interposition material for occupying at least a portion of a space that results from the excision of the trapezium bone.

16. The method according to claim 15, wherein the arm is threaded through the interposition material prior to securing the middle portion of the suture construct to the second bone segment.

17. The method according to claim 1, wherein each of the loop arm, free arm, and middle portion of the suture construct comprises two or more suture strands.

* * * * *